US005665723A

United States Patent [19]
Hartman et al.

[11] Patent Number: 5,665,723
[45] Date of Patent: Sep. 9, 1997

[54] FIBRINOGEN RECEPTOR ANTAGONISTS

[75] Inventors: George D. Hartman, Lansdale; John H. Hutchinson, Philadelphia; Wasyl Halczenko, Lansdale, all of Pa.

[73] Assignee: Merck & Co., Inc., Rahway, N.J.

[21] Appl. No.: 460,372

[22] Filed: Jun. 2, 1995

Related U.S. Application Data

[62] Division of Ser. No. 391,851, Feb. 22, 1995.

[51] Int. Cl.$^6$ .................. A61K 31/495; A61K 31/40; C07D 403/00; C07D 405/00
[52] U.S. Cl. .................. 514/255; 514/414; 544/373; 548/454; 548/466; 548/467
[58] Field of Search .............. 544/373; 514/255, 514/414; 548/466, 467, 454

[56] References Cited

U.S. PATENT DOCUMENTS

| | | | |
|---|---|---|---|
| 3,322,631 | 5/1967 | Sprague et al. | 167/65 |
| 4,010,274 | 3/1977 | Giraldi et al. | 424/274 |
| 4,122,255 | 10/1978 | Krapcho | 542/421 |
| 4,243,807 | 1/1981 | Friebe et al. | 546/232 |
| 4,313,947 | 2/1982 | Nakagawa et al. | 424/248.54 |
| 4,622,331 | 11/1986 | Jozic | 514/331 |
| 5,030,654 | 7/1991 | Barnish et al. | 514/510 |
| 5,227,490 | 7/1993 | Hartman et al. | 514/317 |
| 5,260,316 | 11/1993 | Van Duzer et al. | 514/309 |
| 5,264,420 | 11/1993 | Duggan et al. | 514/19 |
| 5,272,158 | 12/1993 | Hartman et al. | 514/323 |
| 5,281,585 | 1/1994 | Duggan et al. | 514/79 |
| 5,292,756 | 3/1994 | Duggan et al. | 514/331 |
| 5,294,616 | 3/1994 | Duggan et al. | 514/223 |
| 5,321,034 | 6/1994 | Duggan et al. | 514/323 |
| 5,334,596 | 8/1994 | Hartman et al. | 514/301 |
| 5,358,956 | 10/1994 | Hartman et al. | 514/331 |

FOREIGN PATENT DOCUMENTS

| | | |
|---|---|---|
| 0 229 391 A1 | 7/1987 | European Pat. Off. . |
| 0 332 528 A1 | 9/1989 | European Pat. Off. . |
| 0 352 249 A1 | 1/1990 | European Pat. Off. . |
| 0 372 486 A2 | 6/1990 | European Pat. Off. . |
| 0 381 033 A1 | 8/1990 | European Pat. Off. . |
| 0 384 362 A2 | 8/1990 | European Pat. Off. . |
| 0 405 537 A1 | 1/1991 | European Pat. Off. . |
| 0 540 334 A1 | 5/1993 | European Pat. Off. . |
| 2 612 185 A1 | 9/1988 | France . |

*Primary Examiner*—Mukund J. Shah
*Assistant Examiner*—Brenda Coleman
*Attorney, Agent, or Firm*—Richard S. Parr; Mel Winokur

[57] ABSTRACT

Fibrinogen receptor antagonists having the formula for example

21 Claims, No Drawings

FIBRINOGEN RECEPTOR ANTAGONISTS

This is a division of application Ser. No. 08/391,851 filed Feb. 22, 1995.

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between nonterminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661, 111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.*, 262, 16157–16163 (1987); Huang et al., *Biochemistry* 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. The application PCT/US90/02746 describes the use of antibody-poly-peptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidino-piperidine-3-carboxylglycyl-L-aspartyl-L-valine that inhibit platelet aggregation and thrombus formation in mammalian blood. The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibrinogen receptor antagonists. Eur. Pat. App. No. 90101404.3 discloses compounds of the $R^1$-A-$(W)_a$-X-$(CH_2)_b$-$(Y)_c$-$\beta$-Z-COOR wherein $R^1$ is a gnandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

A fibrinogen receptor antagonist of the following formula $$X-Y-\boxed{\begin{array}{c}K\\O\\Z\end{array}\begin{array}{c}\\\\L\end{array}}-A-B$$

and pharmaceutically acceptable salts thereof, where
X is chosen from the group consisting of:

$$-NR^1R^2, \quad -NR^1-\overset{NR^2}{\underset{\|}{C}}-R^1, \quad -\overset{NR^3}{\underset{\|}{C}}-NHR^4, \quad -NR^1-\overset{NR^2}{\underset{\|}{C}}-NR^3R^4,$$

[phenyl with $CH_2NR^2R^3$ substituent],

[phenyl with $-\overset{NR^2}{\underset{R^1}{N}}-\overset{}{C}-NHR^3$ substituent],

[phenyl with $-\overset{NR^1}{\underset{}{C}}-NHR^2$ substituent], and a 5- to 6-membered mono- or bicyclic aromatic or nonaromatic ring system containing 0,1, or 2 heteroatoms selected from N, O and S and either unsubstituted or substituted with $R^1$, $R^2$, $R^3$ or $R^4$.

wherein $R^1$, $R^2$, $R^3$ and $R^4$ are independently selected from the group consisting of hydrogen,
$C_{1-10}$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, $C_{1-4}$ alkylthio $C_{0-6}$ alkyl, aryl $C_{0-4}$ thio $C_{0-6}$ alkyl, carboxy $C_{0-6}$ alkyloxy, and hydroxy $C_{0-6}$ alkyl;

Z is chosen from the group consisting of:
—$CR^1$=$CR^2$—,
—$CR^1$=N—,
—N=$CR^1$—, and
S, O, and $NR^1$;

Y and A are independently chosen from the group consisting of $$-(CH_2)m-, \quad -(CH_2)_m\overset{O}{\underset{\|}{C}}NR^3(CH_2)n-, \quad -(CH_2)_m NR^3\overset{O}{\underset{\|}{C}}(CH_2)n-,$$

-continued $-(CH_2)_mO(CH_2)n-$, $-(CH_2)_m\overset{O}{\underset{\|}{C}}(CH_2)_n-, \quad -(CH_2)_m\overset{S}{\underset{\|}{C}}(CH_2)_n-, \quad -(CH_2)_mSO_2(CH_2)_n-,$ $-(CH_2)_mS(CH_2)_n-, \quad -(CH_2)_mSO(CH_2)_n-,$ $-(CH_2)_mSO_2NR^3(CH_2)_n-, \quad -(CH_2)_mNR^3SO_2(CH_2)-,$ $-(CH_2)_mCR^3=CR^4(CH_2)_n-, \quad -(CH_2)_mC\equiv C(CH_2)_n-,$ $-(CH_2)_m\underset{OH}{\underset{|}{CH}}(CH_2)_n-, \text{ and } -(CH_2)_m aryl(CH_2)_n-,$ $-(CH_2)_mNR^3(CH_2)_n-, \text{ and } -(CH_2)_mNR^3(CH_2)_n-,$ where m and n are integers independently chosen from 0–6, wherein A is attached to a ring atom of the ring comprising K and L, and Y is attached to a ring atom of the ring comprising Z;

K and L are independently chosen from the group consisting of:

$-(CH_2)_m\overset{O}{\underset{\|}{C}}(CH_2)_n-, \quad -(CH_2)_m\overset{O}{\underset{\|}{C}}NR^1(CH_2)_n-,$ $-(CH_2)_mNR^1\overset{O}{\underset{\|}{C}}(CH_2)_n- \quad (CH_2)_mS(CH_2)_n-,$ $-(CH_2)_mSO(CH_2)_n-, \quad -(CH_2)_mSO_2(CH_2)_n-,$ $-(CH_2)_mSO_2NR^1(CH_2)_n-, \quad -(CH_2)_mNR^1SO_2(CH_2)_n-,$ $-(CH_2)_m-, \quad -(CH_2)_m-CH=CH-(CH_2)_n-,$ $-(CH_2)_mO(CH_2)_n, \quad -CH=N-, \quad -N=CH-,$ $-CH_2NR^1-, \text{ and } -NR^1CH_2-;$ B is chosen from the group consisting of:

[structure with $R^6$, $R^7$, $R^5$, $R^8$, $R^9$, N, and $(CH_2)_m-\overset{O}{\underset{\|}{C}}-R^{10}$] and

[structure with $R^6$, $R^7$, $R^5$, $R^8$, $R^9$, N, and $(CH_2)_m-\overset{O}{\underset{\|}{C}}-R^{10}$]

where m=0–2, and
where $R_5$, $R_6$, $R_7$, $R_8$ and $R_9$ are independently chosen from the group consisting of:
hydrogen, fluorine, $C_{1-8}$ alkyl, hydroxyl, —$C_{0-6}$ alkyl—CH=CH—C—$C_{0-6}$ alkyl —$C_{0-6}$ alkyl—CH=CH—C—$C_{0-6}$ alkylaryl —$C_{0-6}$ alkyl—C—=C—$C_{0-6}$ alkyl —$C_{0-6}$ alkyl—C—=C—$C_{0-6}$ alkylaryl hydroxy $C_{1-6}$ alkyl, carboxy $C_{0-6}$ alkyl, $C_{1-6}$ alkyloxy, $C_{3-8}$ cycloalkyl, aryl $C_{1-6}$ alkyloxy, aryl $C_{0-6}$ alkyl, $C_{1-6}$ alkylcarbonyloxy, $C_{0-6}$ alkylamino $C_{0-6}$ alkyl, aryl $C_{0-6}$ alkylamino $C_{0-6}$ alkyl, $C_{0-6}$ dialkylamino $C_{0-6}$ alkyl, aryl $C_{0-6}$ alkylcarbonyloxy, $C_{1-8}$ alkylsulfonylamino $C_{0-6}$ alkyl, $C_{1-6}$ alkylaminocarbonyloxy, aryl $C_{0-6}$ alkylaminocarbonyloxy, aryl $C_{0-8}$ alkylsulfonylamino $C_{0-6}$ alkyl, $C_{1-8}$ alkyloxycarbonylamino $C_{0-8}$ alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl, $C_{0-8}$ alkylaminocarbonyl $C_{0-6}$ alkyl, and aryl $C_{0-8}$ alkylaminocarbonyl $C_{0-6}$ alkyl, unsubstituted or substituted with one or more substituents selected from $R^1$ and $R^2$, and

C—AA, where AA is an L- or D-amino acid, or its corresponding ester, connected through an amide linkage;
$R^{10}$ is chosen from the group consisting of:
hydroxy, $C_{1-8}$ alkyloxy, aryl $C_{0-6}$ alkyloxy, $C_{1-8}$ alkylcarbonyloxy $C_{1-4}$ alkyloxy, aryl $C_{1-8}$ alkylcarbonyloxy $C_{1-4}$ alkyloxy, $C_{1-8}$ alkylaminocarbonyl $C_{1-4}$ alkyloxy, $C_{1-8}$ dialkylaminocarbonyl $C_{1-4}$ alkyloxy, and an L- or D-amino acid joined by an amide linkage, wherein the carboxylic acid moiety of said amino acid is as the free acid or is esterified by $C_{1-6}$ alkyl.

DETAILED DESCRIPTION OF THE INVENTION

A fibrinogen receptor antagonist of the following formula

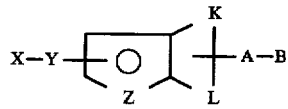

and pharmaceutically acceptable salts thereof, where
X is chosen from the group consisting of:

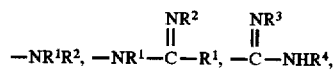

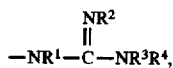

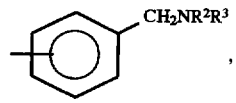

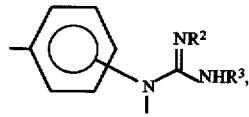

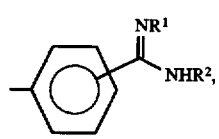

and a 5- to 6-membered mono- or bicyclic aromatic or nonaromatic ring system containing 0,1, or 2 heteroatoms selected from N, O and S and either unsubstituted or substituted with $R^1$, $R^2$, $R^3$ or $R^4$.
$R^1$, $R^2$, $R^3$ and $R^4$ are independently selected from the group consisting of hydrogen,
$C_{1-10}$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, $C_{1-4}$ alkylthio $C_{0-6}$ alkyl, aryl $C_{0-4}$ thio $C_{0-6}$ alkyl, carboxy $C_{0-6}$ alkyloxy, and hydroxy $C_{0-6}$ alkyl;
Z is chosen from the group consisting of:
—$CR^1=CR^2$—, —$CR^1=N$—, —$N=CR^1$—, and S, O, and $NR^1$;
Y and A are independently chosen from the group consisting of

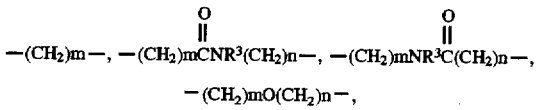

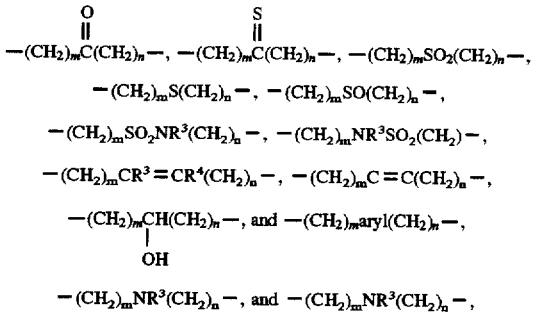

where m and n are integers independently chosen from 0–6, wherein A is attached to a ring atom of the ring comprising K and L, and Y is attached to a ring atom of the ring comprising Z;
K and L are independently chosen from the group consisting of:

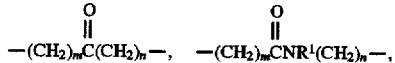

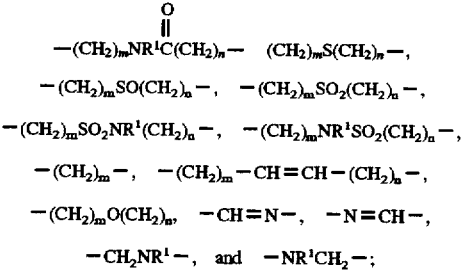

B is chosen from the group consisting of:

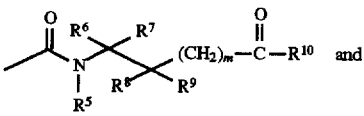

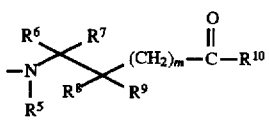

where m=0–2, and
where $R_5$, $R_6$, $R_7$, $R_8$ and $R_9$ are independently chosen from the group consisting of:
hydrogen, fluorine, $C_{1-8}$ alkyl, hydroxyl, —$C_{0-6}$ alkyl—CH=CH—C—$C_{0-6}$ alkyl —$C_{0-6}$ alkyl—CH=CH—C—$C_{0-6}$ alkylaryl —$C_{0-6}$ alkyl—C==C—$C_{0-6}$ alkyl —$C_{0-6}$ alkyl—C==C—$C_{0-6}$ alkylaryl hydroxy $C_{1-6}$ alkyl, carboxy $C_{0-6}$ alkyl, $C_{1-6}$ alkyloxy, $C_{3-8}$ cycloalkyl, aryl $C_{1-6}$ alkyloxy, aryl $C_{0-6}$ alkyl, $C_{1-6}$ alkylcarbonyloxy, $C_{0-6}$ alkylamino $C_{0-6}$ alkyl, aryl $C_{0-6}$ alkylamino $C_{0-6}$ alkyl, $C_{0-6}$ dialkylamino $C_{0-6}$ alkyl, aryl $C_{0-6}$ alkylcarbonyloxy, $C_{1-8}$ alkylsulfonylamino $C_{0-6}$ alkyl, $C_{1-6}$ alkylaminocarbonyloxy, aryl $C_{0-6}$ alkylaminocarbonyloxy, aryl $C_{0-8}$ alkylsulfonylamino $C_{0-6}$ alkyl, $C_{1-8}$ alkyloxycarbonylamino $C_{0-8}$ alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl, $C_{0-8}$ alkylaminocarbonyl $C_{0-6}$ alkyl, and aryl $C_{0-8}$ alkylaminocarbonyl $C_{0-6}$ alkyl, unsubstituted or substituted with one or more substituents selected from $R^1$ and $R^2$, and

C—AA, where AA is an L- or D-amino acid, or its corresponding ester, connected through an amide linkage;
$R^{10}$ is chosen from the group consisting of:
hydroxy, $C_{1-8}$ alkyloxy, aryl $C_{0-5}$ alkyloxy, $C_{1-8}$ alkylcarbonyloxy $C_{1-4}$ alkyloxy, aryl $C_{1-8}$ alkylcarbonyloxy $C_{1-4}$ alkyloxy, $C_{1-8}$ alkylaminocarbonyl $C_{1-4}$ alkyloxy, $C_{1-8}$ dialkylaminocarbonyl $C_{1-4}$ alkyloxy, and an L- or D-amino acid joined by an amide linkage, wherein the carboxylic acid moiety of said amino acid is as the free acid or is esterified by $C_{1-6}$ alkyl.

In one embodiment, compounds of the invention have the formula

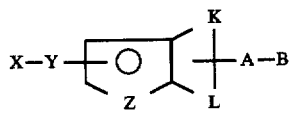

and pharmaceutically acceptable salts thereof, where X is chosen from the group consisting of:

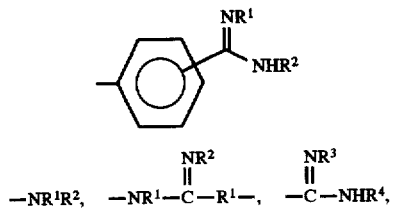

and a 5- to 6- membered mono- or bicyclic nonaromatic ring system containing 0, 1, or 2 heteroatoms selected from N, O, and S and either unsubstituted or substituted with $R^1$, $R^2$, $R^3$ and $R^4$, wherein $R^1$, $R^2$, $R^3$ and $R^4$ are independently selected from the group consisting of hydrogen, $C_{1-10}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy hydroxy $C_{0-6}$ alkyl $C_{1-4}$ alkythio $C_{0-6}$ alkyl, aryl $C_{0-4}$ thio $C_{0-6}$ alkyl, amino $C_{0-3}$ alkyl, $C_{1-6}$ alkylamino $C_{0-3}$ alkyl, and $C_{1-6}$ acylamino $C_{0-3}$ alkyl;
Y and A are independently chosen from the group consisting of:

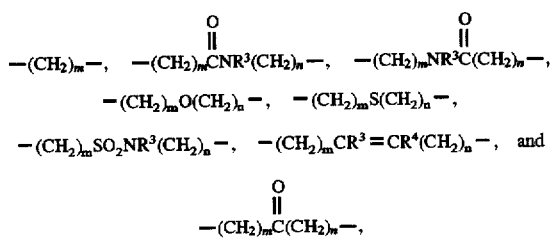

where m and n are integers independently chosen from 0–6, wherein A is attached to a ring atom of the ring comprising K and L, and Y is attached to a ring atom of the ring comprising Z.

In a class of the embodiment, compounds of the invention have the formula

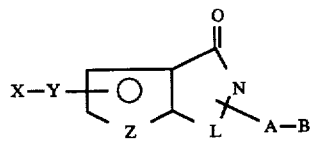

and pharmaceutically acceptable salts thereof, where Z is chosen from the group consisting of:
—$CR^1=CR^2$—, —C=$NR^1$—, —N=$CR^1$—, and S
Y and A are independently chosen from the group consisting of:

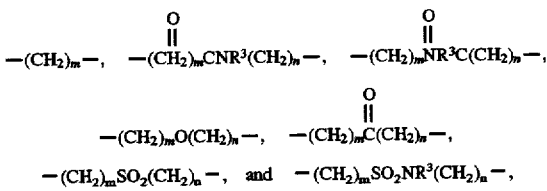

where m and n are integers independently chosen from 0–6, wherein A is attached to a ring atom of the ring comprising L, and Y is attached to a ring atom of the ring comprising Z;
B is chosen from the group consisting of:

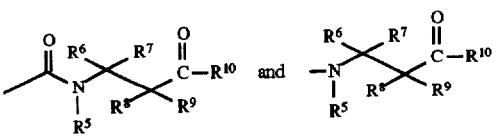

where $R^5$, $R^6$, $R^7$, $R^8$ and $R^9$ are independently chosen from: hydrogen, flourine, $C_{1-8}$ alkyl, hydroxyl, hydroxy $C_{1-6}$ alkyl, —$C_{0-6}$ alkyl —CH=CH—$C_{0-6}$ alkyl, —$C_{0-6}$ alkyl —CH=CH—$C_{0-6}$ alkylaryl, —$C_{0-6}$ alkyl —C≡C—$C_{0-6}$ alkyl, —$C_{0-6}$ alkyl —C≡C—$C_{0-6}$ alkylaryl, carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, aryl $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl; and $R^{10}$ is chosen from the group consisting of: hydroxy, $C_{1-8}$ alkyloxy, and aryl $C_{0-6}$ alkyloxy.

In a subclass of the class of the embodiment, compounds have the formula

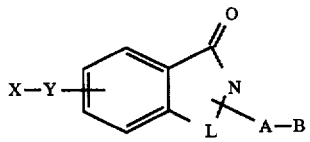

and pharmaceutically acceptable salts thereof, where
L is chosen from the group consisting of:
—$CH_2$— or —$(CH_2)_2$—;
Y and A are independently chosen from the group consisting of:

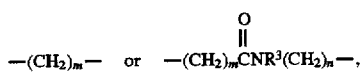

where m and n are integers independently chosen from 0–6, wherein A is attached to a ring atom of the ring comprising L;
B is chosen from the group consisting of:

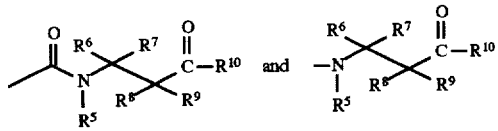

where $R^5$, $R^6$, $R^7$, $R^8$ and $R^9$ are independently chosen from: hydrogen, flourine, $C_{1-8}$ alkyl, hydroxyl, hydroxy $C_{1-6}$ alkyl, —$C_{0-6}$ alkyl —CH=CH—$C_{0-6}$ alkyl, —$C_{0-6}$ alkyl —CH=CH—$C_{0-6}$ alkylaryl, —$C_{0-6}$ alkyl —C≡C—$C_{0-6}$ alkyl, —$C_{0-6}$ alkyl —C≡C—$C_{0-6}$ alkylaryl, carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, aryl $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl; and $R^{10}$ is chosen from the group consisting of:
hydroxy, $C_{1-8}$ alkyloxy, and aryl $C_{0-6}$ alkyloxy.

In a group of the subclass, compounds have the formula

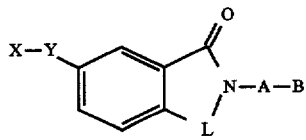

and pharmaceutically acceptable salts thereof, where
X is a 6-membered monocyclic nonaromatic ring containing 0, 1 or 2N heteroatoms either unsubstituted or substituted with $R^1$, $R^2$, $R^3$ or $R^4$, wherein $R^1$, $R^2$, $R^3$ and $R^4$ are independently selected from the group consisting of hydrogen,
$C_{1-10}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy hydroxy $C_{0-6}$ alkyl $C_{1-4}$ alkythio $C_{0-6}$ alkyl, aryl $C_{0-4}$ thio $C_{0-6}$ alkyl, amino $C_{0-3}$ alkyl, $C_{1-6}$ alkylamino $C_{0-3}$ alkyl, and $C_{1-6}$ acylamino $C_{0-3}$ alkyl;

L is chosen from the group consisting of:
—$CH_2$— or —$(CH_2)_2$—;
Y and A are independently chosen from the group consisting of:

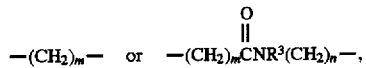

where m and n are integers independently chosen from 0–6;
B is chosen from the group consisting of:

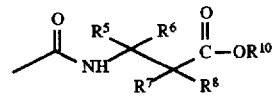

where $R^5$, $R^6$, $R^7$, $R^8$ and $R^9$ are independently chosen from: hydrogen, flourine, $C_{1-8}$ alkyl, hydroxyl, hydroxy $C_{1-6}$ alkyl, —$C_{0-6}$ alkyl —CH=CH—$C_{0-6}$ alkyl, —$C_{0-6}$ alkyl —CH=CH—$C_{0-6}$ alkylaryl, —$C_{0-6}$ alkyl —C≡C—$C_{0-6}$ alkyl, —$C_{0-6}$ alkyl —C≡C—$C_{0-6}$ alkylaryl, carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, aryl $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl; and $R^{10}$ is chosen from the group consisting of:
hydroxy, $C_{1-8}$ alkyloxy, and aryl $C_{0-6}$ alkyloxy.

In a subgroup of the group, compounds have the formula

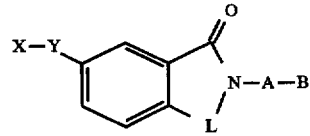

and pharmaceutically acceptable salts thereof, where
X is a 6-membered monocyclic nonaromatic ring containing 0, 1 or 2N heteroatoms either unsubstituted or substituted with $R^1$, $R^2$, $R^3$ or $R^4$, wherein $R^1$, $R^2$, $R^3$ and $R^4$ are independently selected from the group consisting of hydrogen,
$C_{1-10}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy hydroxy $C_{0-6}$ alkyl $C_{1-4}$ alkythio $C_{0-6}$ alkyl, aryl $C_{0-4}$ thio $C_{0-6}$ alkyl, amino $C_{0-3}$ alkyl, $C_{1-6}$ alkylamino $C_{0-3}$ alkyl, and $C_{1-6}$ acylamino $C_{0-3}$ alkyl;

L is chosen from the group consisting of: —$CH_2$— or —$(CH_2)_2$—;

Y and A are independently chosen from the group consisting of:

—$(CH_2)_m$—.

where m is an integer independently chosen from 0 and 1;
B is chosen from the group consisting of:

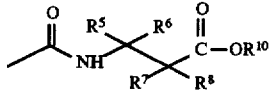

where $R^5$, $R^6$, $R^7$, $R^8$, and $R^9$ are independently chosen from:

hydrogen, flourine, $C_{1-8}$ alkyl, hydroxyl, hydroxy $C_{1-6}$ alkyl,

—$C_{0-6}$ alkyl —CH=CH—$C_{0-6}$ alkyl, —$C_{0-6}$ alkyl —CH=CH—$C_{0-6}$ alkylaryl, —$C_{0-6}$ alkyl —C≡C—$C_{0-6}$ alkyl, —$C_{0-6}$ alkyl —C≡C—$C_{0-6}$ alkylaryl, carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, aryl $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl; and $R^{10}$ is chosen from the group consisting of:
hydroxy, $C_{1-8}$ alkyloxy, and aryl $C_{0-6}$ alkyloxy.

The following compounds were tested and found to inhibit platelet aggregation with $IC_{50}$ values between about 0.01 μM and 100 μM.

N-{[7-(piperazin-1-yl)-3,4-dihydro-1(1H)-isoquinolinone-2-yl]acetyl}-3(S)-(3-pyridyl)-β-alanine, N-{[7-(piperazin-1-yl)-3,4-dihydro-1(1H)-isoquinolinone-2-yl]acetyl}-3(R)-methyl-β-alanine, N-{[7-(piperazin-1-yl)-3,4-dihydro-1(1H)-isoquinolinone-2-yl]acetyl}-β-alanine, N-{[7-(piperazin-1-yl)-3,4-dihydro-1(1H)-isoquinolinone-2-yl]acetyl}-3(R)-(2-phenethyl)-β-alanine, N-{[7-(piperazin-1-yl)-3,4-dihydro-1(1H)-isoquinolinone-2-yl]acetyl}-2(S)-(phenylsulfonylamino)-β-alanine, N-{[7-(piperazin-1-yl)-3,4-dihydro-1(1H)-isoquinolinone-2-yl]acetyl}-2(R)-(phenylsulfonylamino)-β-alanine, N-{[6-(piperazin-1-yl)-2,3-dihydro-1(1H)-isoindolone-2-yl]acetyl}-3(R)-methyl-β-alanine, N-{[7-(piperazin-1-yl)-3,4-dihydro-1(1H)-isoquinolinone-2-yl]acetyl}-3(R)-(2-chlorobenzyl)-β-alanine, N-{[7-(4-benzylpiperazin-1-yl)-3,4-dihydro-1(1H)-isoquinolinone-2-yl]acetyl}-3(R)-(2-chlorobenzyl)-β-alanine, N-{[7-(piperazin-1-yl)-3,4-dihydro-1(1H)-isoquinolinone-2-yl]acetyl}-3-(3-fluorophenyl)-β-alanine, N-{[7-(piperazin-1-yl)-3,4-dihydro-1(1H)-isoquinolinone-2-yl]acetyl}-3(R)-(ethynyl)-β-alanine, N-{[7-(Piperazin-1-yl)-3,4-dihydro-1(1H)-isoquinolinone-2-yl]acetyl}-3(S)-(3-pyridyl)-β-alanine ethyl ester, N-{[6-(Piperazin-1-yl)-2,3-dihydro-1(1H)-isoindolone-2-yl]acetyl}-3(R)-methyl-13-alanine n-butyl ester, N-{[7-(Piperazin-1-yl)-3,4-dihydro-1(1H)-isoquinolinone-2-yl]acetyl}-3(R)-methyl-β-alanine ethyl ester, N-{[7-(4-Benzylpiperazin-1-yl)-3,4-dihydro-1(1H)-isoquinolinone-2-yl]acetyl}-3(R)-2(2-chlorobenzyl)-β-alanine ethyl ester, and N-{[7-(Piperazin-1-yl)-3,4-dihydro-1(1H)-isoquinolinone-2-yl]acetyl}-3(R)-(ethynyl)-β-alanine ethyl ester.

Platelet aggregation is measured at 37° C. in a Chronolog aggregometer. The reaction mixture contains gel-filtered human platelets ($2\times10^8$ per ml), fibrinogen (100 micrograms per ml (ug/ml)), $Ca^{2+}$(1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celcius unless otherwise noted.

In addition to the following preparative procedures, several examples of in-vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, mate, tartrate, teoclate, tosylate, triethiodide, valerate.

The compounds of the present invention may be chiral; included within the scope of the present invention are racemic mixtures and separated enantiomers of formula (I). Furthermore all diastereomers, including E, Z isomers, of formula (I) are included in the present scope. Furthermore, hydrates as well as anhydrous compositions and polymorphs of formula (I) are within the present invention.

Prodrugs, such as ester derivatives of described compounds, are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The term "alkyl" means straight or branched alkane, alkene or alkyne.

The term "aryl" means a 5- or 6-membered aromatic ring containing 0, 1, or 2 heteroatoms selected from O, N, and S.

The terms "alkyloxy" or "alkoxy" include an alkyl portion where alkyl is as defined above.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit.

The term "halogen" includes fluorine, chlorine, iodine and bromine.

The term "oxy" means an oxygen (O) atom. The term "thio" means a sulfur (S) atom. Under standard nomenclature used throughout this disclosure, the terminal portion of the designated side chain is described first followed by the adjacent functionality toward the point of attachment. For example, a $C_{1-6}$ alkyl substituted with $C_{1-5}$ alkylcarbonylamino is equivalent to

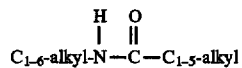

Amino acids suitable for compounds of the present invention include naturally occurring L- or D-amino acids include, for example, those naturally occurring L-amino acids present in humans, e.g. protein amino acids., including L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine, and those naturally occurring D-amino acids which are non-protein amino acids, such as those found, for example, in antibiotic substances produced by bacteria and fungi, including D-valine, D-asparagine, D-glutamate, D-ornithine, D-phenylalanine, D-leucine, D-cysteine, and D-aspartate. (see Zubay "BIOCHEMISTRY" Addison-Wesley Publishing Company, Inc. (Reading, Mass.) 1983 pp. 867–870 and Stryer "BIOCHEMISTRY" W. H. Freeman and Company (New York, N.Y.) 3rd Edition 1988 pp. 16–21).

In the schemes and examples below, various reagent symbols have the following meanings:

| | |
|---|---|
| BOC(or Boc): | t-butyloxycarbonyl. |
| Pd-C: | Palladium on activated carbon catalyst. |
| DMF: | Dimethylformamide. |
| DMSO: | Dimethylsulfoxide. |
| CBZ: | Carbobenzyloxy. |
| $CH_2Cl_2$: | Methylene chloride. |
| $CHCl_3$: | chloroform. |
| EtOH: | ethanol. |
| MeOH: | methanol. |
| NBS: | N-bromosuccinimide |
| EtOAc: | ethyl acetate. |
| HOAc: | acetic acid. |
| EDC: | 1-(3-Dimethylaminopropyl)-3-ethylcarbodiimide hydrochloride. |
| NaHMDS | sodium bis(trimethylsilyl)amide. |
| HOBT | 1-Hydroxybenzotriazole hydrate. |
| TFA | Trifluoroacetic acid. |
| LDA: | Lithium diisopropylamide. |

X, a terminal basic moiety of compound of the invention, is exemplified by heterocyclic rings such as

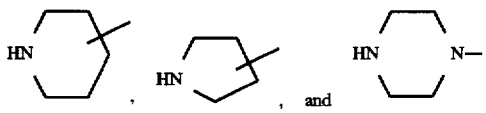

and heteroaromatic rings such as

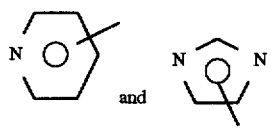

as well as amino, amidino, and guanadino moieties.

The compounds of the present invention can be administered in such oral froms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thrombo-embolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of adminstration; the renal and hepatic function of the patient; and the particular compound or salt thereof employed. An ordinarilly skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. Intravenously, the most prefered doses will range from about 0.1 to about 10 mg/kg/minute during a constant rate infusion. Advantageously, compounds of the present invention may be administered in divided doses of two, three, or four times daily. Furthermore, preferred compounds for the present invention can be adminstered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittant throughout the dosage regime.

In the methods of the present invention, the compounds herein described in detail can form the active ingredient, and are typically administered in admixture with suitable pharmaceutical diluents, excipients or carders (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylkcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carders to which the compound molecules are coupled. The compounds of the present invention may also be coupled with soluble polymers as targetable drug cariers. Such polymers can include polyvinylpyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anticoagulation agents or thrombolytic agents such as plasminogen activators or streptokinase to acheive synergistic effects in the treatment of various vascular pathologies. They may also be combined with heparin, aspirin, or warfarin.

SCHEME I

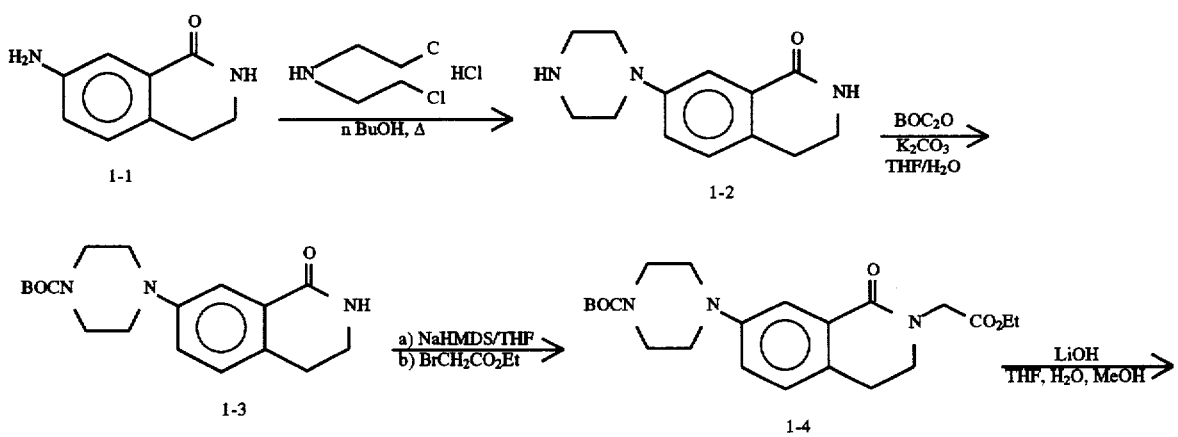

-continued
SCHEME I

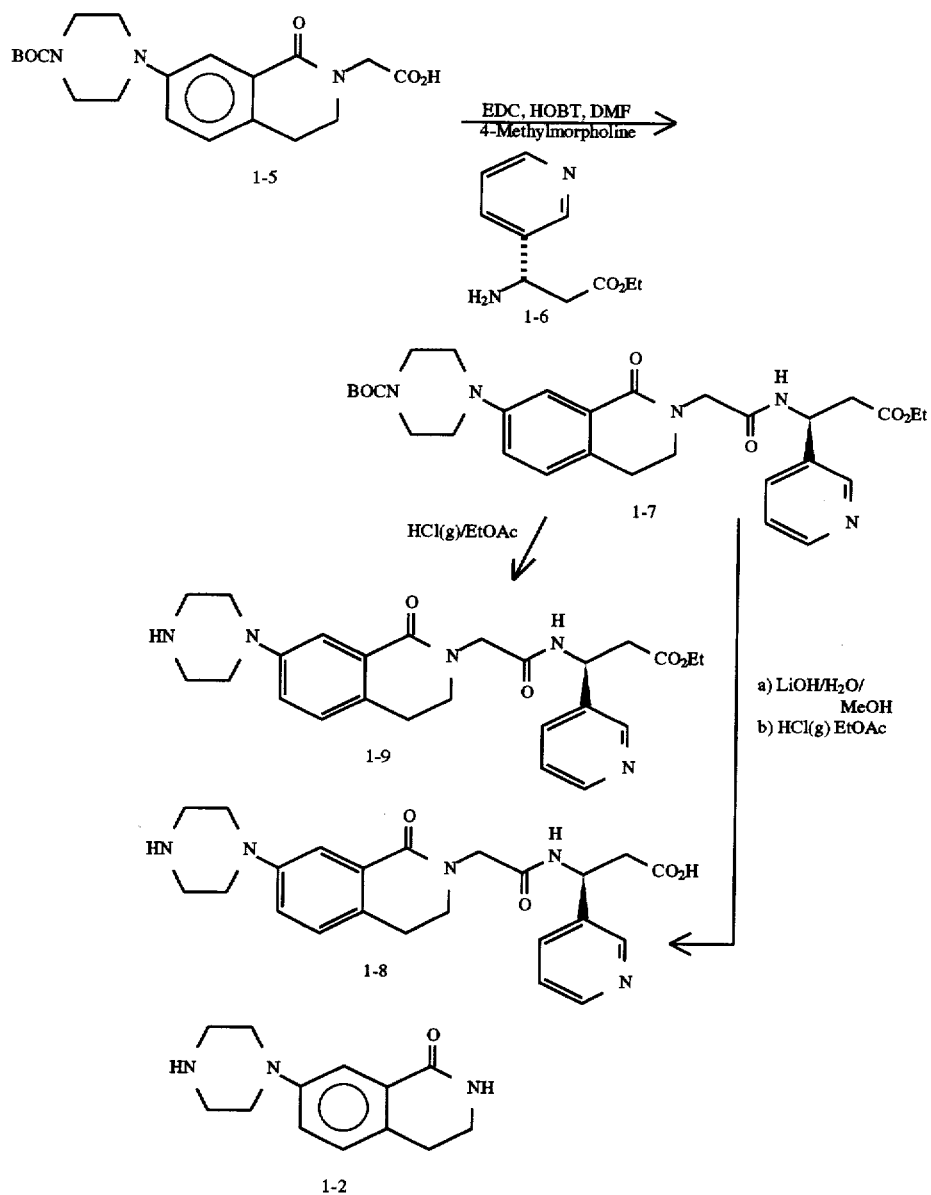

7-(Piperazin-1-yl)-3,4-dihydro-1(1H)-isoquinolinone (1-2)

A solution of 7-amino-3,4-dihydro-1(1H)-isoquinolone (1-1)(Girard et al, *J. Org. Chem.*, 1983, vol. 48, p. 3220; 5.0 g, 30.8 mmol) and bis(2-chloroethyl)amine hydrochloride (6.3 g, 33.9 mmol) in n-butanol (250 mL) was stirred at 110° C. for 3 days. The precipitate was removed by filtration to provide the starting amine as the HCl salt (3.6 g). Evaporation of the n-butanol under reduced pressure afforded a dark oil which was purified by column chromatography (silica gel; EtOH/H$_2$O/NH$_4$OH 10:0.5:0.5) to give 1-2. $^1$H NMR (CD$_3$OD): δ2.86 (2H, t), 3.10 (4H, m), 3.22 (4H, m), 3.44 (2H, t), 7.18 (2H, m), 7.55 (1H, m).

7-(4-t-Butoxycarbonylpiperazin-1-yl)-3,4-dihydro-1 (1H)isoquinolinone (1-3)

7-(Piperazin-1-yl)-3,4-dihydro-1(1H)-isoquinolinone (1-2) (2.22 g, 9.61 mmol), Boc$_2$O (2.30 g, 10.6 mmol) and K$_2$CO$_3$ (1.33 g, 9.61 mmol) were stirred in THF (20 mL) and H$_2$O (20 mL) for 24 hours. The solution was poured into water and extracted with EtOAc (3x), washed with water then brine, dried (MgSO$_4$) and evaporated. Chromatography of the residue (EtOAc) gave a yellow solid which was swished with ether to afford 1-3 as a white solid. R$_f$ (silica, EtOAc)=0.32.

Ethyl[7-(4-t-butoxycarbonylpiperazin-1-yl)-3,4-dihydro-1(1H)-isoquinolinone-2-yl]acetate (1-4)

A solution of 7-(4-t-butoxycarbonylpiperazin-1-yl)-3,4-dihydro-1(1H)-isoquinolinone (1-3) (2.37 g, 7.16 mmol) in THF (30 mL) at −78° C. under argon was treated with NaHMDS (1M solution in THF; 7.88 mL, 7.88 mmol) and the temperature was allowed to rise to −50° C. over 30 minutes. The solution was cooled back to −78° C. and ethyl bromoacetate (1.19 mL, 10.7 mmol) was added in one lot.

[7-(4-t-Butoxycarbonylpiperazin-1-yl)-3,4-dihydro-1(1H)-isoquinolinone-2-yl]acetic acid (1-5)

Ethyl [7-(4-t-butoxycarbonylpiperazin-1-yl)-3,4-dihydro-1(1H)-isoquinolinone-2-yl]acetate (1-4) (2.9 g, 6.95 mmol), 1N LiOH (20.9 mL, 20.9 mmol) and MeOH (50 mL) were stirred for 16 hours at room temperature. The solvent was removed, the residue was taken up in EtOAc and washed with 1N HCl. Repeated extraction of the aqueous phase followed by washing of the bulked organic layers with brine (5 mL), drying (MgSO$_4$) and evaporation afforded 1-5 as a solid. $^1$H NMR (CD$_3$OD): d1.48 (9H, s), 2.99 (2H, t), 3.20 (4H, m), 3.62 (6H, m), 4.31 (2H, s), 7.22 (2H, s), 7.60 (1H, s).

N-{[7-(4-t-Butoxycarbonylpiperazin-1-yl)-3,4-dihydro-1(1H)-isoquinolinone-2-yl]acetyl}-3(S)-(3-pyridyl)-β-alanine ethyl ester (1-7)

A solution of [7-(4-t-butoxycarbonylpiperazin-1-yl)-3,4-dihydro-1(1H)-isoquinolinone-2-yl]acetic acid (1-5) (195 mg, 0.5 mmol), ethyl 3-amino-3(S)-(3-pyridyl)propionate dihydrochloride (1-6) (Rico et al, *J. Org. Chem.* 1993, vol. 58, p. 7948; 127 mg, 0.55 mmol), EDC (105 mg, 0.55 mmol), HOBT (74 mg, 0.55 mmol) and 4-methylmorpholine (0.12 mL, 1.1 mmol) in DMF (5 mL) was stirred at room temperature for 16 hours. The mixture was diluted with EtOAc and water and- the pH adjusted to ~pH 7 with 1N LiOH. The solution was extracted with EtOAc (3x), dried (MgSO$_4$) and the solvent removed in vacuo. Purification of the residue by column chromatography (10% MeOH in EtOAc) gave 1-7. R$_f$ (silica, 10% MeOH in EtOAc)=0.43.

N-{[7-(Piperazin-1-yl)-3,4-dihydro-1(1H)-isoquinolinone-2-yl]acetyl}-3(S)-(3-pyridyl)-β-alanine (1-8)

The ester 1-7 (77 mg, 0.14 mmol) was hydrolysed with 1N LiOH (0.41 mL, 0.41 mmol) and MeOH (2 mL) for 16 hours. The solvent was removed, the residue was suspended in EtOAc and H$_2$O and HCl gas was bubbled into the mixture. After 30 minutes, the solvent was removed in vacuo and the crude product was then purified by reverse phase HPLC (C18 column, H$_2$O/CH$_3$CN with 0.1% TFA, gradient) to give 1-8 as the TFA salt.
FAB mass spectrum m/z=438 (M+1)
Anal. Calcd for C$_{23}$H$_{27}$N$_5$O$_4$·2.65 TFA·2.0 H$_2$O C, 43.82: H, 4.37; N, 9.03 found C, 43.84; H, 4.39; N, 9.18

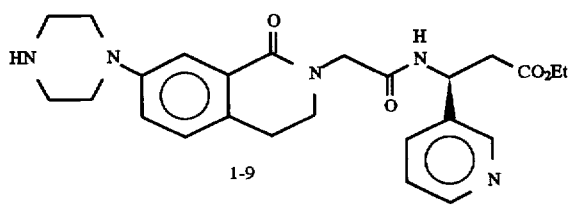

1-9

N-{[7-(Piperazin-1-yl)-3,4-dihydro-1(1H)-isoquinolinone-2-yl]acetyl}-3(S)-(3-pyridyl)-β-alanine ethyl ester (1-9)

N-{[7-(4-t-Butoxycarbonylpiperazin-1-yl)-3,4-dihydro-1(1H)-isoquinolinone-2-yl]acetyl}-3(S)-(3-pyridyl)-β-alanine ethyl ester (1-7), (140 mg) was dissolved in 10 ml EtOAc and HCl gas bubbled through until the solution was saturated. After stirring for 1 hour, the solvent was removed and the residue purified by reverse phase HPLC (C18 colunto, H$_2$O/CH$_3$CN with 0.1% TFA, gradient) to give 1-9 as the TFA salt.
FAB mass spectrum m/z=466 (M+1)
Anal. Calcd for C$_{25}$H$_{31}$N$_5$O$_4$·3.85 TFA·2.0 H$_2$O C, 41.75: H, 4.16; N, 7.45 found C, 41.75; H, 4.00; N, 7.74

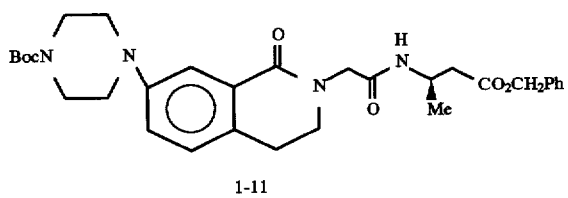

1-11

N-{[7-(4-t-Butoxyccarbonylpiperazin-1-yl)-3,4-dihydro-1(1H)-isoquinolinone-2-yl]acetyl}-3(R)-methyl-β-alanine benzyl ester (1-11)

Following the procedure described for 1-7, but substituting 3(R)-methyl-β-alanine benzyl ester (1-10 Celgene) for ethyl 3-amino-3(S)-(3-pyridyl) propionate dihydrochloride, 1-11 was prepared. $^1$H NMR (CDCl$_3$): δ1.22 (3H, d), 1.49 (9H, s), 2.56 (2H, d), 2.95 (2H, m), 3.15 (4H, m), 3.57 (6H, m), 4.03 (1H, d, J=15 Hz), 4.28 (1H, d, J=15 Hz), 4.48 (1H, m), 5.04 (2H, s), 6.74 (1H, d), 7.07 (1H, dd), 7.13 (1H, d), 7.33 (5H, m), 7.62 (1H, d).

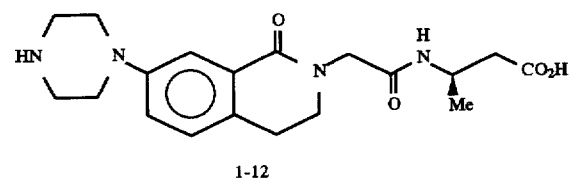

1-12

N-{[7-(Piperazin-1-yl)-3,4-dihydro-1(1H)-isoquinolinone-2-yl]acetyl}-3(R)-methyl-β-alanine (1-12)

Following the procedure described for 1-8, the ester 1-11 was converted into 1-12 as the TFA salt.
FAB mass spectrum m/z=375 (M+1)
Anal. Calcd for C$_{19}$H$_{26}$N$_4$O$_4$·1.45 TFA·1.7 H$_2$O C, 46.11; H, 5.45; N, 9.82 found C, 46.12; H, 5.42; N, 10.13

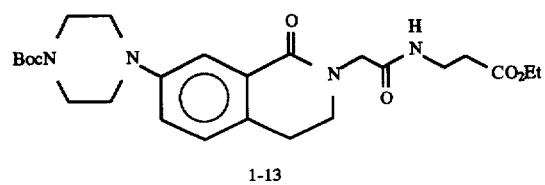

1-13

N-{[7-(4-t-Butoxycarbonylpiperazin-1-yl)-3,4-dihydro-1(1H)-isoquinolinone-2-yl]acetyl}-β-alanine ethyl ester (1-13)

Following the procedure described for 1-7, but substituting β-alanine ethyl ester hydrochloride (Aldrich) for ethyl 3-amino-3(S)-(3-pyridyl)propionate dihydrochloride, the title compound was prepared. R$_f$ (silica, EtOAc)=0.3.

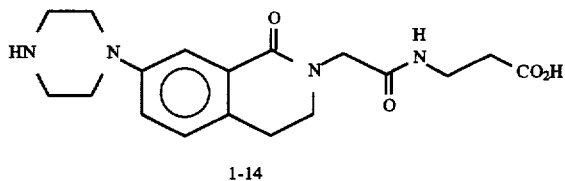

1-14

N-{[7-(Piperain-1-yl)-3,4-dihydro-1(1H)-isoquinolinone-2-yl]acetyl}-β-alanine (1-14)

Following the procedure described for 1-8, the ester 1-12 was converted into 1-14 as the TFA salt.

FAB mass spectrum m/z=361 (M+1)

Anal. Calcd for $C_{18}H_{24}N_4O_4 \cdot 0.65$ TFA·0.9 $H_2O$ C, 45.30; H, 4.90; N, 9.92 found C, 45.29; H, 4.86; N, 10.24

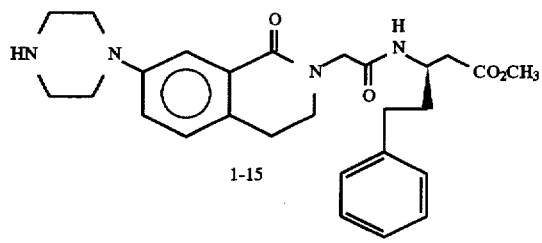

1-15

N-{[7-(4-t-Butoxycarbonylpiperazin-1-yl)-3,4-dihydro-1(1H)-isoquinolinone-2-yl]acetyl}-3(R)-(2-phenethyl)-β-alanine methyl ester (1-15)

Following the procedure described for 1-7, but substituting 3(R)-(2-phenethyl)-β-alanine methyl ester hydrochloride (1 -1 5a) (U.S. Pat. No. 5,281,585) for ethyl 3-amino-3(S)-(3-pyridyl)propionate dihydrochloride, the title compound was prepared. $R_f$ (silica, 10% MeOH in EtOAc) =0.78.

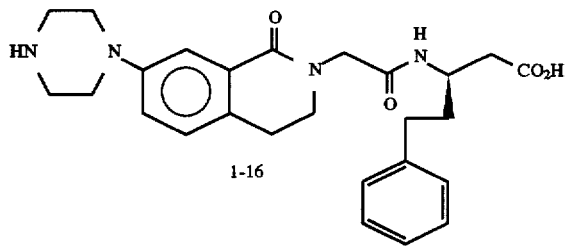

1-16

N-{[7-(Piperazin-1-yl)-3,4-dihydro-1(1H)-isoquinolinone-2-yl]acetyl}-3(R)-(2-phenethyl)-β-alamine (1-16)

Following the procedure described for 1-8, the ester from 1-15 was converted into 1-16 as the TFA salt.

FAB mass spectrum m/z=465 (M+1)

Anal. Calcd for $C_{26}H_{32}N_4O_4 \cdot 2.1$ TFA·1.0 $H_2O$ C, 50.23; H, 5.04; N, 7.76 found C, 50.12; H, 4.93; N, 7.91

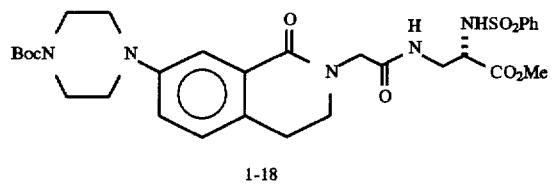

1-18

N-{[7-(4-t-Butoxycarbonylpiperazin-1-yl)-3,4-dihydro-1(1H)-isoquinolinone-2-yl]acetyl}-2(S)-(phenylsulfonylamino)-β-alanine methyl ester (1-18)

Following the procedure described for 1-7, but substituting 2(S)-(phenylsulfonylamino)-β-alanine ethyl ester hydrochloride (1-17) (WO 94/12181) for ethyl 3-amino-3(S)-(3-pyridyl)propionate dihydrochloride, 1-18 was prepared. $R_f$ (silica, EtOAc)=0.37.

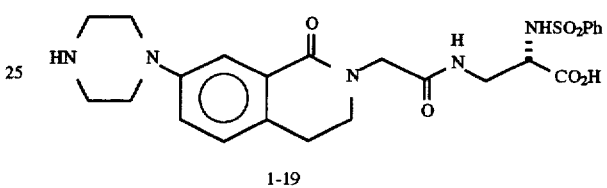

1-19

N-{[7-(Piperazin-1-yl)-3,4-dihydro-1(1H)-isoquinolinone-2-yl]acetyl}-2(S)-phenylsuifonylamino)-β-alanine (1-19)

Following the procedure described for 1-8, the ester 1-18 was converted into 1-19 as the TFA salt.

FAB mass spectrum m/z=516 (M+1)

Anal. Calcd for $C_{24}H_{29}N_5O_6S \cdot 1.7$ TFA·1.0 $H_2O$ C, 45.24; H, 4.53; N, 9.63 found C, 45.22; H, 4.36; N, 9.94

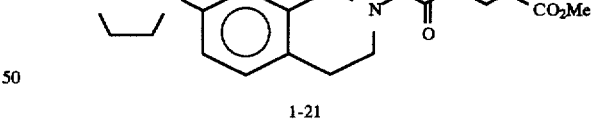

1-21

N-{[7-(4-t-Butoxycarbonylpiperazin-1-yl)-3,4-dihydro-1(1H)-isoquinolinone-2-yl]acetyl }-2(R)-(phenylsulfonylamino)-β-alanine methyl ester (1-21)

Following the procedure described for 1-7, but substituting 2(R)-(phenylsulfonylamino)-β-alanine for ethyl 3-amino-3(S)-(3-pyridyl)propionate dihydrochloride, the title compound was prepared. $^1$H NMR (CD$_3$OD): δ 1.50 (9H, s), 3.00 (2H, m), 3.18 (2H, m), 3.3-3.7 (10H, m), 4.09 (1H, dd), 4.23 (2H, m), 7.2 (2H, m), 7.5-7.6 (4H, m), 7.85 (2H, m), 8.22 (1H, m).

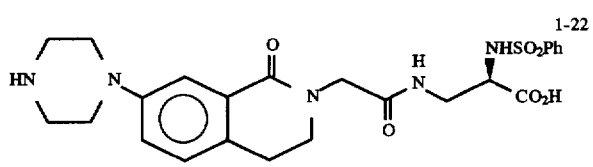

N-{[7-(Piperazin-1-yl)-3,4-dihydro-1(1H)-
isoquinolinone-2-yl]acetyl}-(R)-
(phenylsulfonylamino)-β-alanine (1-22)

Following the procedure described for 1-8, the ester 1-21 was converted into 1-22 and was purified by reverse phase HPLC (C18 column, H₂O/CH₃CN with 0.1% TFA, gradient) to give the 1-22 as the TFA salt.

FAB mass spectrum m/z=516 (M+1)

Anal. Calcd for $C_{24}H_{29}N_5O_6S \cdot 2.0$ TFA·1.75H₂O C, 43.39; H, 4.49; N, 9.03 found C, 43.36; H, 4.16; N, 9.26

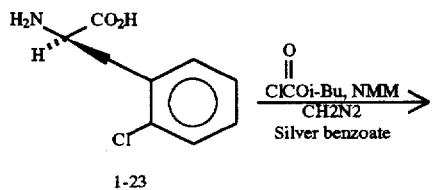

3(R)-(2-Chlorobenzyl)-β-alanine ethyl ester
hydrochloride (1-24)

N-BOC-D-3-(2-chlorophenyl)alanine 1-23 (Synthetech, 3.0 g, 10 mmol) in EtOAc (80 mL) at 0° C. was heated with N-methylmorpholine (1.32 mL, 12 mmol) and isobutylchloroformate (1.6 mL, 12 mmol) and stirred for 3 hours. The solution was poured into H₂O, extracted with EtOAc (x 2), washed with brine, dried (MgSO₄) and the solvent removed to give an oil. The oil was heated with excess ethereal diazomethane for 30 minutes, then the solution was purged with argon and evaporated to give a yellow oil.

To this yellow oil was added EtOH (80 mL), Et₃N (1.6 mL, 12 mmol) and then silver benzoate (700 mg, 4 mmol). After stirring for 30 minutes the solution was concentrated and the crude product was purified by silica gel chromatography (eluting with 15% EtOAc in hexane) to give a white solid (1.1 g).

Deprotection of the resulting solid using HCl in EtOAc afforded 1-24 as a waxy solid (945 mg). $R_f$ (silica; 10% MeOH in CH₂Cl₂)=0.53.

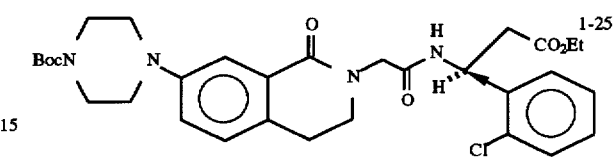

N-{[7-(4-t-Butoxycarbonyl piperazin-1-yl)-3,4-
dihydro-1(1H)-isoquinoline-2-yl]acetyl}-3(R)-(2-
chlorobenzyl)-β-alanine ethyl ester (1-25)

Following the procedure described for 1-7 but using 3(R)-(2-chlorobenzyl)-β-alanine ethyl ester hydrochloride (1-24) as starting material, 1-25 was obtained as an oil.

¹H NMR (CDCl₃): δ1.25 (3H, t), 1.50 (9H, s), 2.58 (2H, d), 2.8-3.1 (4H, m), 3.18 (4H, m), 3.3-3.5 (2H, m), 3.6 (4H, m), 4.00 (1H, d), 4.10 (2H, q), 4.21 (1H, d), 4.60 (1H, m), 6.9-7.2 (6H, m), 7.65 (1H, s).

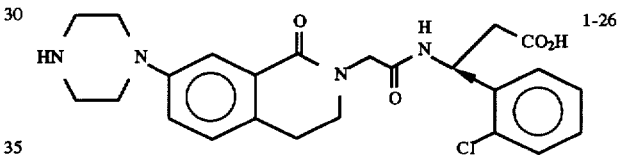

N-{[7-(Piperazin-1-yl)-3,4-dihydro 1(1H)-
isoquinoline-2-yl]acetyl}-(R)-(2-chlorobenzyl)-β-
alanine (1-26)

Following the procedure described for 1-8, 1-25 was converted into the title compound and isolated after reverse phase HPLC as the TFA salt.

FAB mass spectrum m/z=485 (m+1)

Anal. Calcd. for $C_{25}H_{29}N_4O_4Cl \cdot 1.9$ TFA C, 49.30; H, 4.44; N, 7.99 found C, 49.03; H, 4.45; N, 8.34

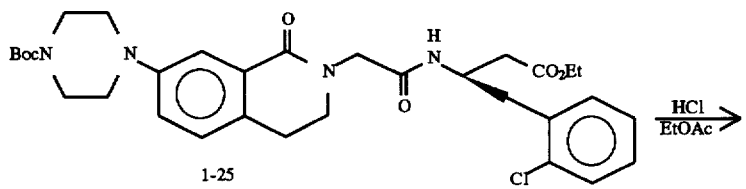

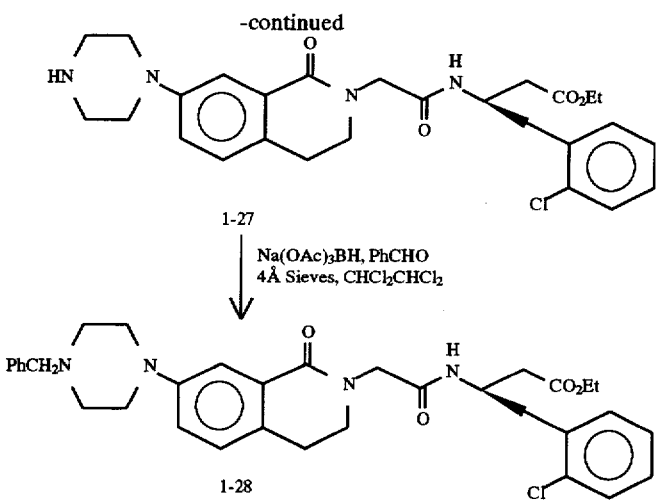

N-{[7-(4-Benzylpiperazin-1-yl)-3,4-dihydro-1(1H)-isoquinolinone-2-yl]acetyl}-3(R)-(2-chlorobenzyl)-β-alanine ethyl ester (1-28)

N-{[7-(4-t-butoxycarbonylpiperazin-1-yl)-3,4-dihydro-1(1H)-isoquinolinone-2-yl]acetyl}-3(R)-(2-chlorobenzyl)-β-alanine ethyl ester (1-25) (212 mg, 0.35 mmol) was treated with HCl/EtOAc to give the corresponding deprotected compound 1-27.

To this compound (100 mg, 0.18 mmol) in 1,2-dichloroethane (4 mL) was added 4 Å sieves, benzaldehyde (22.2 μL, 0.22 mmol), sodium triacetoxyborohydride (116 mg, 0.55 mmol) and Et$_3$N (25.4 μL, 0.18 mmol) and the mixture was stirred for 16 hours at room temperature. After filtration through celite, the solution was poured into saturated NaHCO$_3$, extracted with EtOAc (x2), washed with brine, dried (MgSO$_4$) and the solvent removed in vacuo. Chromatography of the residue (silica; 5% MeOH in CHCCl$_3$) afforded 1-28 as an oil. R$_f$ (silica; 5% MeOH in CHCl$_3$)=0.5.

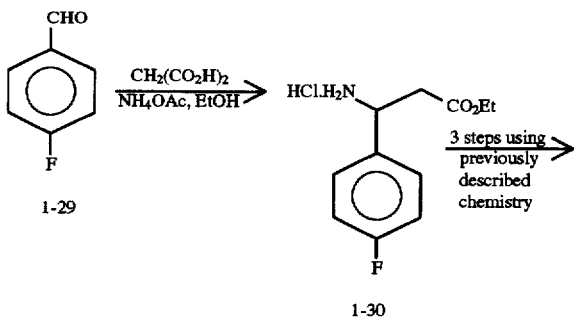

3-(3-Fluorophenyl)-β-alanine ethyl ester hydrochloride (1-30)

A solution of malonic acid (2.9 g, 27.8 mmol), 4-fluorobenzaldehyde 1-29 (2.6 mL, 24.2 mmol) and NH$_4$OAc (2.42 g, 31.4 mmol) in EtOH (80 mL) was heated at reflux for 16 hours. The mixture was cooled and the precipitate was collected by filtration and washed with cold EtOH to give a white solid (1.9 g).

This solid (1.9 g) was dissolved in EtOH (100 mL) and HCl (g) was bubbled through the solution for 10 minutes. After stirring for 24 hours, the solvent was removed to provide 1-30. $^1$H NMR (CD$_3$OD): δ 1.19 (3H, t), 2.99 (1H, dd), 3.08 (1H, dd), 4.17 (2H, q), 4.75 (! H, t) 7.15-7.35 (3H, m), 7.5 (1H, m).

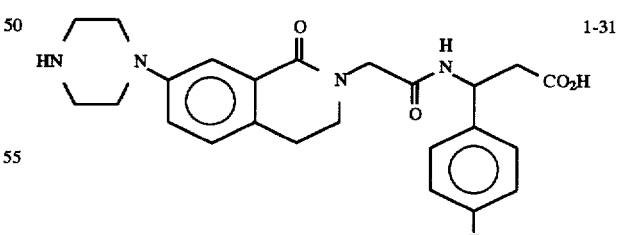

N-{[7-(Piperazin-1-yl)-3,4-dihydro-1(1H)-isoquinolinone-2-yl]acetyl}-3-(3 -fluorophenyl)-β-alanine (1-31)

Following the procedure of 1-7 and 1-8, but using 3-(3-fluorophenyl)-β-alanine ethyl ester hydrochloride 1-30 as starting material, 1-31 was obtained as the TFA salt.
FAB mass spectrum m/z=455 (m+1).

Anal. Calcd. for $C_{24}H_{27}N_4O_4F \cdot 1.6$ TFA C, 51.29; H, 4.53; N, 8.80 found C, 51.34; H, 4.48; N, 8.80
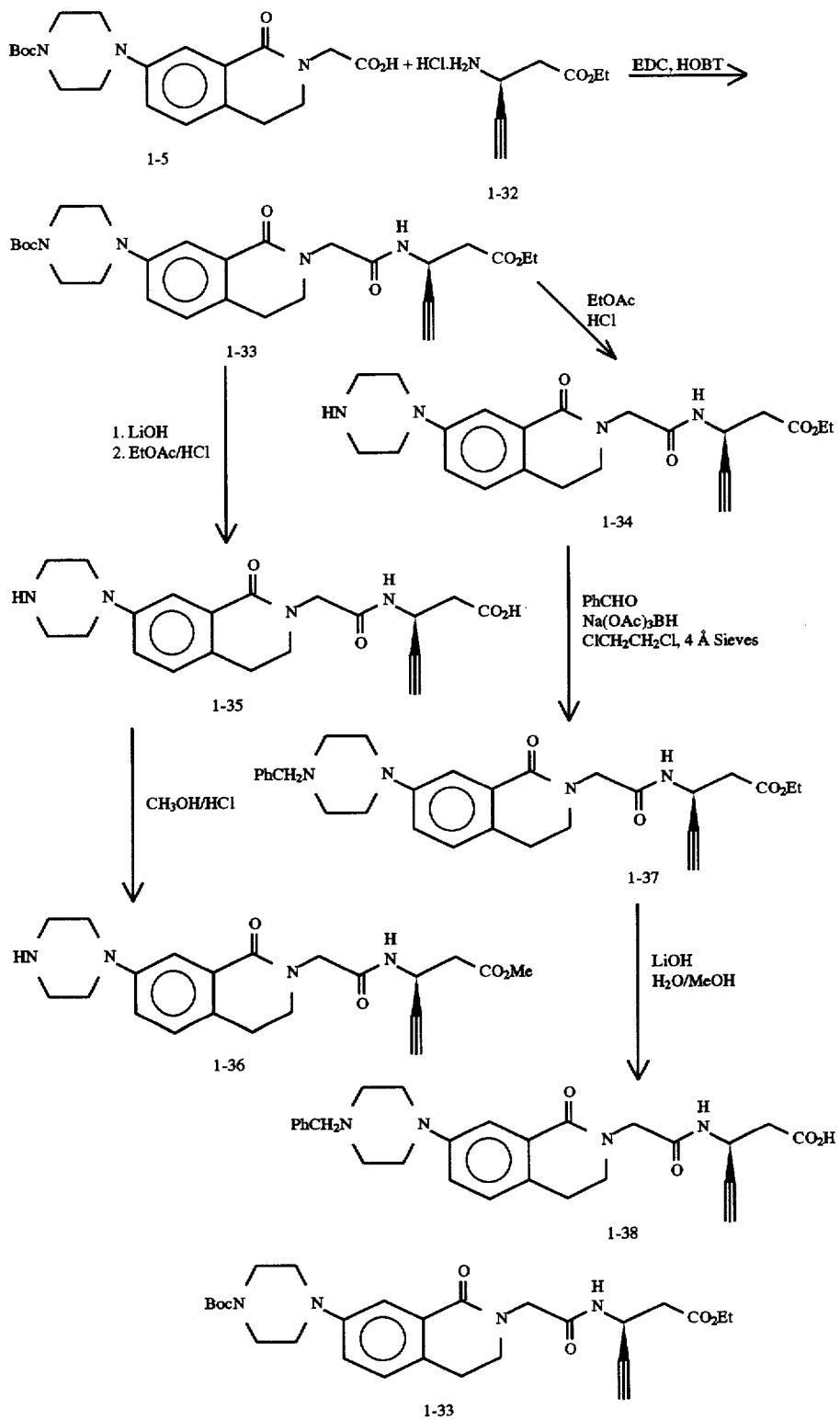

N-{[7-(4-N-Boc-Piperazin-1-yl)-3,4-dihydro-1(1H)-isoquinolinone-2-yl]acetyl}-3(S)-(ethynyl)-β-alanine ethyl ester (1-33)

To a solution of 1-5 (150 mg, 0.39 mmol), HOBT (63 mg, 0.46 mmol) and EDC (111 mg, 0.58 mmol) was added 3(S)-(ethynyl)-β-alanine ethyl ester hydrochloride (1-32) (U.S. Pat. No. 5,272,162; 82 mg, 0.46 mmol) and Et$_3$N (80.7 gl, 0.58 mmol). The mixture was stirred at room temperature under argon for 16 hours and then partitioned between EtOAc and 10% citric acid. The aqueous phase was extracted with EtOAc (x3) and the combined organic layers then washed with saturated aqueous NaHCO$_3$ followed by brine. Removal of the dried (MgSO$_4$) solvent afforded a yellow oil which was purified by column chromatography (silica gel; hexane/EtOAc 1:1) to give 1-33 as an oil. R$_f$ (silica; EtOAc/hexane 2:1) 0.57

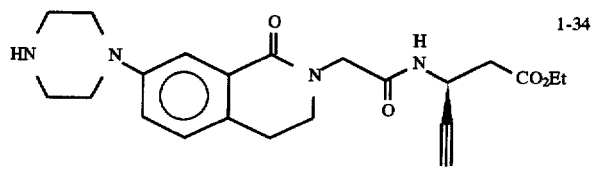

N-{[7-(Piperazin-1-yl)-3,4-dihydro-1(1H)-isoquinolinone-2-yl]acetyl}-3(S)-(ethynyl)-β-alanine ethyl ester (1-34)

HCl (g) was bubbled through a solution of 1-33 (176 mg, 0.37 mmol) in 50 ml of EtOAc for 5 minutes. The solvent was removed in vacuo to leave 1-34 as the HCl salt.
FAB mass spectrum m/z=413 (m+1).

Anal. calcd. for C$_{22}$H$_{28}$N$_4$O$_4$ 2.65 HCl C, 51.89; H, 6.07; N, 11.00 found C, 51.93; H, 6.04; N, 10.70

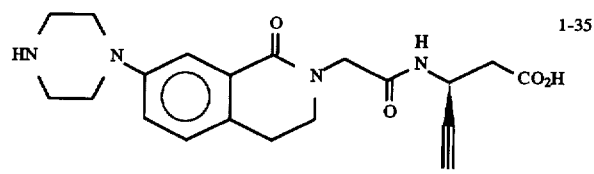

N-{[7-(Piperazin-1-yl)-3,4-dihydro-1(1H)-isoquinolinone-2-yl]acetyl}-3(S)-(ethynyl)-β-alanine (1-35)

The ester 1-33 (70 mg, 0.16 mmol) was stirred in 10 ml MeOH and 0.65 ml 1N LiOH for 16 hours and then 1N HCl was added to give pH=4. After removal of the solvent the residue was purified by reverse phase HPLC (C$_{18}$ column, H$_2$O/CH$_3$CN with 0.1% TFA, gradient) to give 1-35 as the TFA salt.

FAB mass spectrum m/z=385 (m+1)

Anal. calcd. for C$_{20}$H$_{24}$N$_4$O$_4$ 1.6•TFA C, 49.16; H, 4.55; N, 9.88 found C, 49.06; H, 4.59; N, 10.07

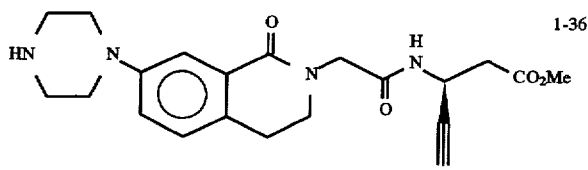

N-{[7-(Piperazin-1-yl)-3,4-dihydro-1(1H)-isoquinolinone-2-yl]acetyl}-3(S)-(alkynyl)-β-alanine methyl ester (1-36)

A solution of 1-35 in methanol was treated with HCl gas. After 1 hour, the solvent was removed and the residue was purified by reverse phase HPLC (C$_{18}$ column, H$_2$O/CH$_3$CN with 0.1% TFA, gradient) to give 1-36 as the TFA salt.

FAB mass spectrum m/z=399 (m+1)

Anal. calcd. for C$_{21}$H$_{26}$N$_4$O$_4$•1.80 TFA C, 48.94; H, 4.64; N, 9.28 found C, 48.94; H, 4.72; N, 9.31

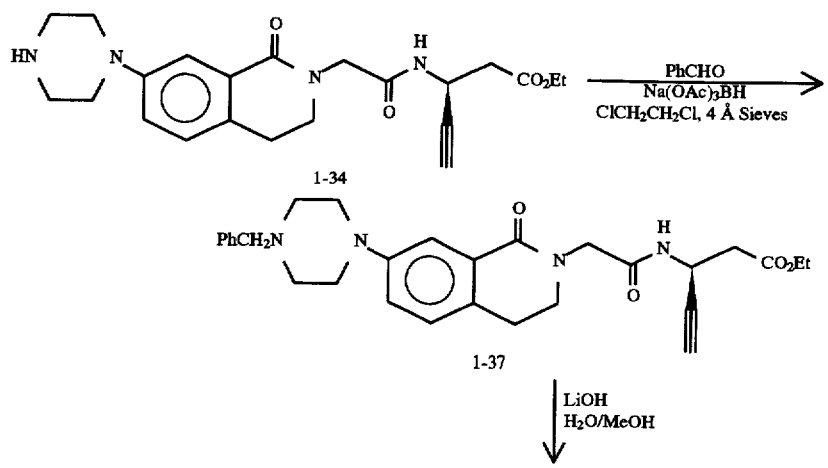

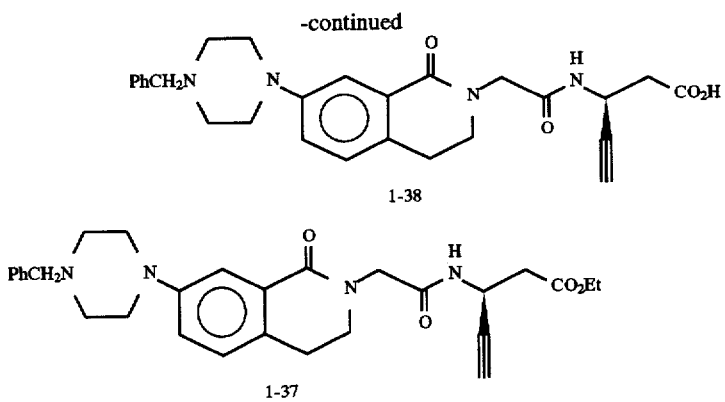

N-{[7-(4-Benzylpiperazin-1-yl)-3,4-dihydro-1(1H)-isoquinolinone-2-yl]acetyl}-3(S)-(alkynyl)-β-alanine ethyl ester (1-37)

A solution of 1-34 (213 mg, 0.48 mmol), benzaldehyde (58 μL, 0.57 mmol), NaBH (OAc)$_3$ (303 mg, 1.43 mmol) and Et$_3$N (66.5 μL, 0.48 mmol) in 1,2-dichloroethane (4 ml) with 4 Å molecular sieves was stirred for 3 days. The mixture was filtered through celite, poured into NaHCO$_3$ (saturated solution) and extracted with EtOAc (x2). After washing the organic layers with brine, drying (MgSO$_4$) and filtration the solvent was removed to give an oil. Purification by silica gel chromatography (EtOAc) afforded 1-37 which was converted to the HCl salt by treatment with 0.1% HCl solution and then lyophilization.

FAB mass spectrum m/z=503 (m+1)

Anal. calcd. for C$_{29}$H$_{34}$N$_4$O$_4$·1.6 HCl C, 62.09; H, 6.40; N, 9.99 found C, 62.15; H, 6.35; N, 9.77.

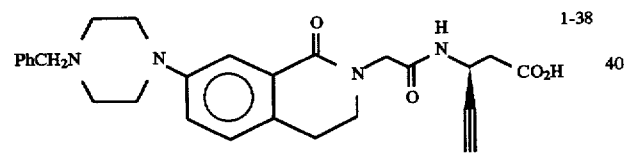

N-{[7-(4-Benzylpiperazin-1-yl)-3,4-dihydro-1(1H)-isoquinolinone-2-yl]acetyl}-3(S)-(alkynyl)-β-alanine (1-38)

1-37 was hydrolysed in aqueous LiOH/NaOH according to the procedure dscribed for 1-5. Purification by reverse phase HPLC (C$_{18}$ column; H$_2$O/CH$_3$CN with 0.1% TFA, gradient) to give 1-38 as the TFA salt.

FAB mass spectrum m/z=475 (m+1)

Anal. calcd. for C$_{27}$H$_{30}$N$_4$O$_4$·1.4 TFA

C, 56.44; H, 4.99; N, 8.83 found C, 56.49; H, 5.01; N, 8.86.

SCHEME 2

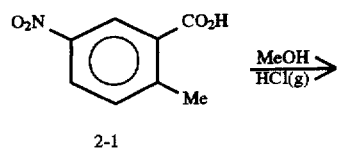

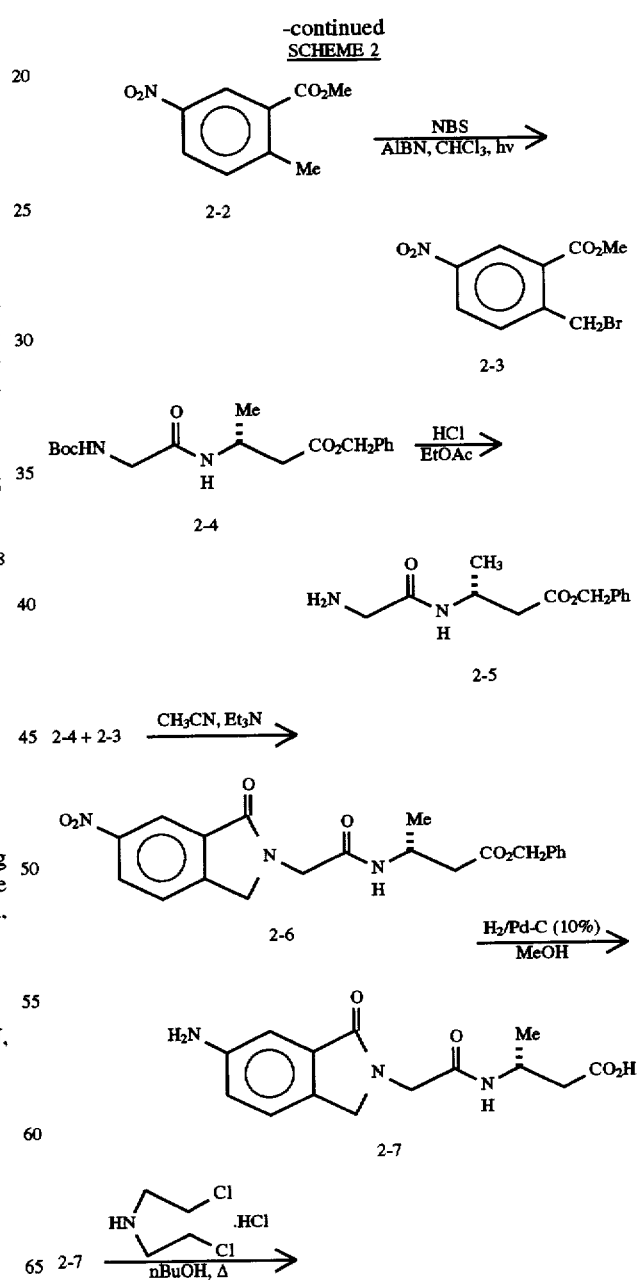

-continued
SCHEME 2

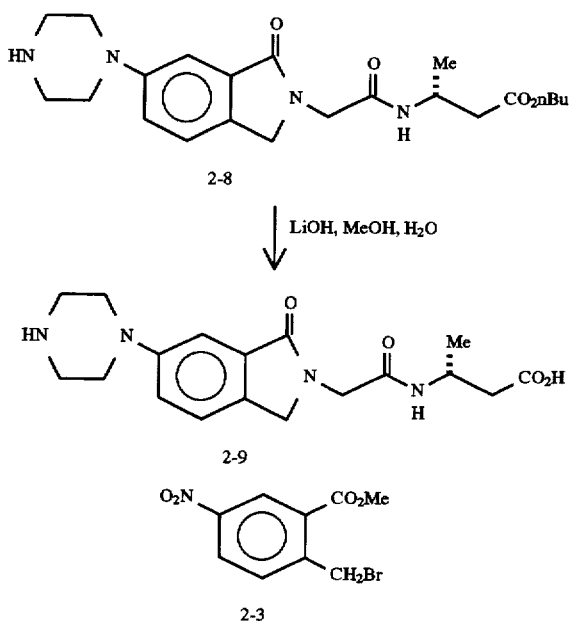

Methyl 6-Bromomethyl-3-nitrobenzoate (2-3)

3-Nitro-6-methylbenzoic acid (2-1) (Aldrich) was converted into methyl 3-nitro-6-methylbenzoate (2-2) using the standard procedure of MeOH and HCl gas. To a mixture of methyl 3-nitro-6-methylbenzoate (2-2) (2.0 g, 10.3 mmol) and N-bromosuccinimide (1.64 g, 9.23 mmol) in CHCl₃ was added AIBN (20 mg) and this was then photolysed at reflux for 4 hours. The reaction was cooled, filtered and the filtrate evaporated to dryness. Chromatography of the residue (silica, hexane/EtOAc 92:8) afforded 2-3 as a solid (1.56 g). R$_f$ (silica; hexane/EtOAc 10:1)=0.25.

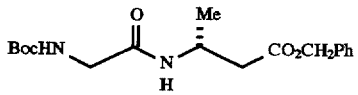

N-t-Butoxycarbonylglycyl-3(R)-methyl-β-alanine benzyl ester (2-4)

N-t-Butoxycarbonylglycine was coupled with 3(R)-methyl-β-alanine benzyl ester • 0.5 H₂SO₄ (1-10) (Celgene) using the conditions described for 1-7, to give 2-4 after chromatography (silica; hexane/EtOAc 2:3). R$_f$ (silica; hexane/EtOAc 1:1)=0.3.

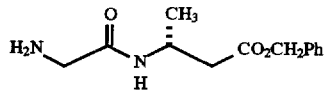

N-Glycyl-3(R)-methyl-β-alanine benzyl ester hydrochloride (2-5)

N-t-Butoxycarbonylglycyl-3(R)-methyl-β-alanine benzyl ester 2-4 (3.32 g) in EtOAc (100 mL) cooled to −60° C. was treated with HCl gas until saturated. The mixture was stirred for 30 minutes then the solvent was removed and the residue triturated with ether to give 2-5 as a solid.

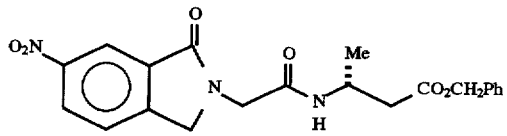

N-{[9-Nitro-2,3-dihydro-1(1H)-isoindolone-2-yl]acetyl}-3(R)-methyl-β-alanine benzyl ester (2-6)

Methyl 6-bromomethyl-3-nitrobenzoate (430 mg, 1.64 mmol), N-glycyl-3(R)-methyl-β-alanine benzyl ester hydrochloride 2-4 (611 mg, 2.13 mmol) and triethylamine (0.68 mL, 4.92 mmol) were stirred in acetonitrile (10 mL) for 16 hours. The solution was poured into 1N HCl and extracted with EtOAc (3x), washed with brine, dried (MgSO₄) and evaporated. Purification by column chromatography eluting with EtOAc afforded 2-6 as a solid. R$_f$ (silica; EtOAc)=0.45.

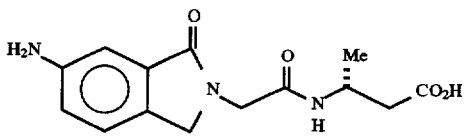

N-{[6-Amino-2,3-dihydro-1(1H)-isoindolone-2-yl]acetyl}-3(R)-methyl-β-alanine (2-7)

A solution of N-{[6-nitro-2,3-dihydro-1(1H)-isoindolone-2-yl]acetyl}-3(R)-methyl-β-alanine benzyl ester (2-6) (374 mg) in MeOH (35 mL) was purged with argon and then 10% Pd on carbon was added. The mixture was placed under an atmosphere of H₂ (balloon) and stirred for 16 hours. After filtration through celite, the solvent was removed to give 2-7 as a solid. FAB mass spectrum m/z=292 (M+1).

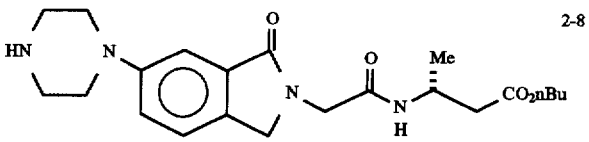

N-{[6-(Piperazin-1-yl)-2,3-dihydro-1(1H)-isoindolone-2-yl]acetyl}-3(R)-methyl-β-alanine n-butyl ester (2-8)

N-{[6-Amino-2,3-dihydro-1(1H)-isoindolone-2-yl]acetyl}-(R)-methyl-β-alanine (2-7) (203 mg, 0.7 mmol) and bis(2-chloroethyl) amine hydrochloride (137 mg, 0.77 mmol) in n-butanol (10 mL) were heated at 110° C. for 3 days. The solvent was removed and the residue chromatographed OEtOH/H₂O/NH₄OH 10:0.5:0.5) to give 2-8. R$_f$ (silica; EtOH/H₂O/NH₄OH 10:0.5:0.5)=0.61.

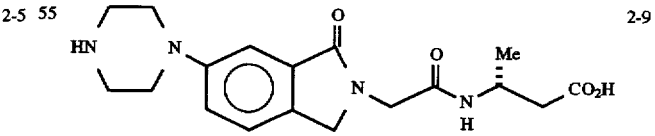

N-{[6-(Piperazin-1-yl)-2,3-dihydro-1(1H)-isoindolone-2-yl]acetyl}-3(R)-methyl-β-alanine (2-9)

The ester 2-8 (150 mg, 0.36 mmol), 1N LiOH (1.08 mL, 1.08 mmol) and MeOH (5 mL) were stirred for 16 hours. The pH was adjusted to ~pH 5 and the MeOH was removed in vacuo to give an aqueous solution which was purified by reverse phase HPLC (C18 column, $H_2O/CH_3CN$ with 0.1% TFA, gradient) to give 2-9 as the TFA salt.

FAB mass spectrum m/z=361 (M+1)

Anal. Calcd for $C_{18}H_{24}N_4O_4 \cdot 2.0$ TFA$\cdot 1.6$ $H_2O \cdot 0.3$ $CH_3CN$ C, 43.11; H, 4.82; N, 9.57 found C, 43.10; H, 4.76; N, 9.71

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

What is claimed is:

1. A fibrinogen receptor antagonist of the following formula

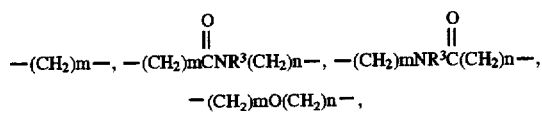

and pharmaceutically acceptable salts thereof, where X is

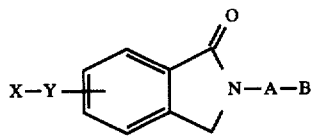

wherein $R^1$ is selected from the group consisting of hydrogen, $C_{1-10}$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, $C_{1-4}$ alkylthio $C_{0-6}$ alkyl, aryl $C_{0-4}$ thio $C_{0-6}$ alkyl, carboxy $C_{0-6}$ alkyloxy, and hydroxy $C_{0-6}$ alkyl;

Y and A are independently chosen from the group consisting of

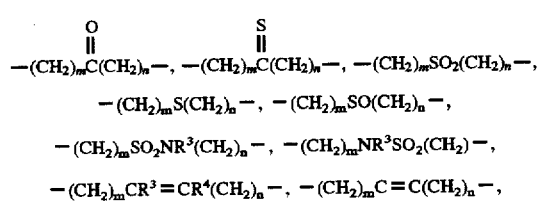

—(CH$_2$)$_m$CH(CH$_2$)$_n$—, and —(CH$_2$)$_m$aryl(CH$_2$)$_n$—,
|
OH

—(CH$_2$)$_m$NR$^3$(CH$_2$)$_n$—, and —(CH$_2$)$_m$NR$^3$(CH$_2$)$_n$—, wherein $R^3$ and $R^4$ are selected from the group consisting of hydrogen, $C_{1-10}$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamine $C_{0-8}$ alkyl, $C_{1-6}$ dialkylamine $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, $C_{1-4}$ alkylthio $C_{0-6}$ alkyl, aryl $C_{0-4}$ thio $C_{0-6}$ alkyl, carboxy $C_{0-6}$ alkyloxy, and hydroxy $C_{0-6}$ alkyl, and where m and n are integers independently chosen from 0–6, wherein and Y is attached to a ring atom of the aromatic six-membered ring;

B is chosen from the group consisting of:

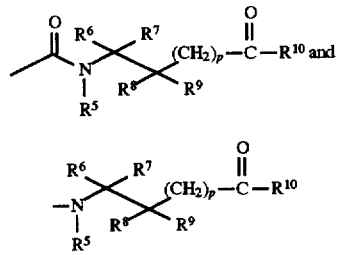

where p=0–2, and where $R_5$, $R_6$, $R_7$, $R_8$ and $R_9$ are independently chosen from the group consisting of: hydrogen, fluorine, $C_{1-8}$ alkyl, hydroxyl, $C_{0-6}$ alkyl—CH=CH—$C_{1-6}$ alkyl $C_{0-6}$ alkyl—CH=CH$_2$ $C_{0-6}$ alkyl—CH=CH—$C_{0-6}$ alkylaryl $C_{0-6}$ alkyl—C≡C—$C_{1-6}$ alkyl $C_{0-6}$ alkyl≡C—CH $C_{0-6}$ alkyl—C≡C—$C_{0-6}$ alkylaryl hydroxy $C_{1-6}$ alkyl, carboxy $C_{0-6}$ alkyl, $C_{1-6}$ alkyloxy, $C_{3-8}$ cycloalkyl, aryl $C_{1-6}$ alkyloxy, aryl $C_{0-6}$ alkyl, $C_{1-6}$ alkylcarbonyloxy, $C_{0-6}$ alkylamino $C_{0-6}$ alkyl, aryl $C_{0-6}$ alkylamino $C_{0-6}$ alkyl, $C_{0-6}$ dialkylamino $C_{0-6}$ alkyl, aryl $C_{0-6}$ alkylcarbonyloxy, $C_{1-8}$ alkylsulfonylamino $C_{0-6}$ alkyl, $C_{1-6}$ alkylaminocarbonyloxy, aryl $C_{0-6}$ alkylaminocarbonyloxy, aryl $C_{0-8}$ alkylsulfonylamino $C_{0-6}$ alkyl, $C_{1-8}$ alkyloxycarbonylamino $C_{0-8}$ alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl, $C_{0-8}$ alkylaminocarbonyl $C_{0-6}$ alkyl, and aryl $C_{0-8}$ alkylaminocarbonyl $C_{0-6}$ alkyl, unsubstituted or substituted with one or more substituents selected from $R^1$, and

where AA is an L- or D-amino acid, or its corresponding ester, connected through an amide linkage;

$R^{10}$ is chosen from the group consisting of:

hydroxy, $C_{1-8}$ alkyloxy, aryl $C_{0-6}$ alkyloxy, $C_{1-8}$ alkylcarbonyloxy $C_{1-4}$ alkyloxy, aryl $C_{1-8}$ alkylcarbonyloxy $C_{1-4}$ alkyloxy, $C_{1-8}$ alkylaminocarbonyl $C_{1-4}$ alkyloxy, $C_{1-8}$ dialkylaminocarbonyl $C_{1-4}$ alkyloxy, and an L- or D-amino acid joined by an amide linkage, wherein the carboxylic acid moiety of said amino acid is as the free acid or is esterified by $C_{1-6}$ alkyl.

2. A compound of claim 1 having the formula and pharmaceutically acceptable salts thereof, where X is wherein $R^1$ is selected from the group consisting of hydrogen, $C_{1-10}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy hydroxy $C_{0-6}$ alkyl $C_{1-4}$ alkylthio $C_{0-6}$ alkyl, aryl $C_{0-4}$ thio $C_{0-6}$ alkyl, amino $C_{0-3}$ alkyl, $C_{1-6}$ alkylamino $C_{0-3}$ alkyl, and $C_{1-6}$ acylamino $C_{0-3}$ alkyl;

Y and A are independently chosen from the group consisting of:

$$-(CH_2)_m-, \quad -(CH_2)_m\overset{O}{\overset{\|}{C}}NR^3(CH_2)_n-, \quad -(CH_2)_mNR^3\overset{O}{\overset{\|}{C}}(CH_2)_n-,$$

$$-(CH_2)_mO(CH_2)_n-, \quad -(CH_2)_mS(CH_2)_n-,$$

$$-(CH_2)_mSO_2NR^3(CH_2)_n-, \quad -(CH_2)_mCR^3=CR^4(CH_2)_n-, \text{ and}$$

$$-(CH_2)_m\overset{O}{\overset{\|}{C}}(CH_2)_n-,$$

where m and n are integers independently chosen from 0–6, wherein, and Y is attached to a ring atom of the aromatic six-membered ring.

3. A compound of claim 2 having the formula and pharmaceutically acceptable salts thereof, where Y and A are independently chosen from the group consisting of:

$$-(CH_2)_m-, \quad -(CH_2)_m\overset{O}{\overset{\|}{C}}NR^3(CH_2)_n-, \quad -(CH_2)_mNR^3\overset{O}{\overset{\|}{C}}(CH_2)_n-,$$

$$-(CH_2)_mO(CH_2)_n-, \quad -(CH_2)_m\overset{O}{\overset{\|}{C}}(CH_2)_n-,$$

$$-(CH_2)_mSO_2(CH_2)_n-, \text{ and } -(CH_2)_mSO_2NR^3(CH_2)n-,$$

where m and n are integers independently chosen from 0–6, wherein A is attached to a ring atom of the ring comprising L, and Y is attached to a ring atom of the ring comprising Z;

B is chosen from the group consisting of:

where R5, R6, $R^7$, $R^8$ and $R^9$ are independently chosen from:

hydrogen, flourine, $C_{1-8}$ alkyl, hydroxyl, hydroxy $C_{1-6}$ alkyl, $C_{0-6}$ alkyl—CH=CH—$C_{1-6}$ alkyl, $C_{0-6}$ alkyl—CH=CH$_2$ $C_{0-6}$ alkyl—CH=CH—$C_{0-6}$ alkylaryl $C_{0-6}$ alkyl—C≡C—$C_{1-6}$ alkyl, $C_{0-6}$ alkyl—C≡C—CH —$C_{0-6}$ alkyl —C≡C—$C_{0-6}$ alkylaryl, carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, aryl $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl; and $R^{10}$ is chosen from the group consisting of:
hydroxy, $C_{1-8}$ alkyloxy, and aryl $C_{0-6}$ alkyloxy.

4. A compound of claim 3 having the formula and pharmaceutically acceptable salts thereof, where; Y and A are independently chosen from the group consisting of:

$$-(CH_2)_m- \quad \text{or} \quad -(CH_2)_m\overset{O}{\overset{\|}{C}}NR^3(CH_2)_n-,$$

where m and n are integers independently chosen from 0–6, wherein A is attached to a ring atom of the ring comprising L;

B is chosen from the group consisting of:

where $R^5$, $R^6$, $R^7$, $R^8$ and $R^9$ are independently chosen from:
hydrogen, flourine, $C_{1-8}$ alkyl, hydroxyl, hydroxy $C_{1-6}$ alkyl, $C_{0-6}$ alkyl—CH=CH—$C_{1-6}$ alkyl, $C_{0-6}$ alkyl—CH=CH$_2$ $C_{0-6}$ alkyl—CH=CH—$C_{0-6}$ alkylaryl $C_{0-6}$ alkyl—C=C—$C_{1-6}$ alkyl, $C_{0-6}$ alkyl—C=C—CH $C_{0-6}$ alkyl—C=C—$C_{0-6}$ alkylaryl carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, aryl $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl; and $R^{10}$ is chosen from the group consisting of:
hydroxy, $C_{1-8}$ alkyloxy, and aryl $C_{0-6}$ alkyloxy.

5. A compound of claim 4 having the formula

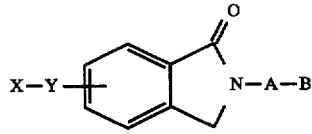

and pharmaceutically acceptable salts thereof, where X is

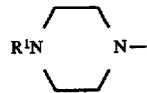

wherein $R^1$ is selected from the group consisting of hydrogen,
$C_{1-10}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy hydroxy $C_{0-6}$ alkyl $C_{1-4}$ alkythio $C_{0-6}$ alkyl, aryl $C_{0-4}$ thio $C_{0-6}$ alkyl, amino $C_{0-3}$ alkyl, $C_{1-6}$ alkylamino $C_{0-3}$ alkyl, and $C_{1-6}$ acylamino $C_{0-3}$ alkyl;

Y and A are independently chosen from the group consisting of:

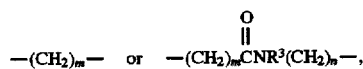

where m and n are integers independently chosen from 0–6, wherein;
B is

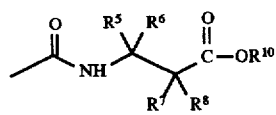

where $R^5$, $R^6$, $R^7$, $R^8$ and $R^9$ are independently chosen from: hydrogen, flourine, $C_{1-8}$ alkyl, hydroxyl, hydroxy $C_{1-6}$ alkyl, $C_{0-6}$ alkyl —CH=CH—$C_{1-6}$ alkyl, $C_{0-6}$ alkyl —CH=CH$_2$, $C_{0-6}$ alkyl—CH=CH—$C_{0-6}$ alkylaryl, $C_{0-6}$ alkyl —C≡C—$C_{1-6}$ alkyl, $C_{0-6}$ alkyl —C≡CH, $C_{0-6}$ alkyl —C≡C—$C_{0-6}$ alkylaryl, carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, aryl $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl; and $R^{10}$ is chosen from the group consisting of:
hydroxy, $C_{1-8}$ alkyloxy, and aryl $C_{0-6}$ alkyloxy.

6. A compound of claim 5 having the formula

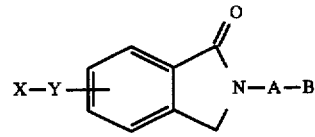

and pharmaceutically acceptable salts thereof, where X is

wherein $R^1$ is selected from the group consisting of hydrogen,
$C_{1-10}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy hydroxy $C_{0-6}$ alkyl $C_{1-4}$ alkythio $C_{0-6}$ alkyl, aryl $C_{0-4}$ thio $C_{0-6}$ alkyl, amino $C_{0-3}$ alkyl, $C_{1-6}$ alkylamino $C_{0-3}$ alkyl, and $C_{1-6}$ acylamino $C_{0-3}$ alkyl;

Y and A are independently chosen from the group consisting of:

—(CH$_2$)$_m$—, where m is an integer independently chosen from 0 and 1, wherein A is attached to a ring atom of the ring comprising L;

B is

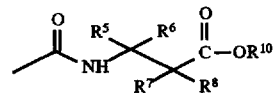

where $R^5$, $R^6$, $R^7$, $R^8$ and $R^9$ are independently chosen from: hydrogen, flourine, $C_{1-8}$ alkyl, hydroxyl, hydroxy $C_{1-6}$ alkyl, $C_{0-6}$ alkyl —CH=CH—$C_{1-6}$ alkyl, $C_{0-6}$ alkyl —CH=CH$_2$, $C_{0-6}$ alkyl —CH=OH—$C_{0-6}$ alkylaryl, $C_{0-6}$ alkyl —C≡C—$C_{1-6}$ alkyl, $C_{0-6}$ alkyl —C≡C—CH, $C_{0-6}$ alkyl —C≡C—$C_{0-6}$ alkylaryl, carboxy $C_{0-6}$ alkyl, $C_{1-6}$ alkyloxy, $C_{3-8}$ cycloalkyl, aryl $C_{0-6}$ alkyl, $C_{1-6}$ alkylcarbonyloxy, $C_{0-6}$ alkylamino $C_{0-6}$ alkyl, aryl $C_{0-6}$ alkylcarbonyloxy, $C_{0-6}$ dialkylamino $C_{0-6}$ alkyl, $C_{1-6}$ alkylaminocarbonyloxy, aryl $C_{1-6}$ alkylaminocarbonyloxy, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-8}$ alkylaminocarbonylamino $C_{0-6}$ alkyl, aryl $C_{0-8}$ alkylaminocarbonylamino $C_{0-6}$ alkyl, $C_{0-8}$ atkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl; and $R^{10}$ is chosen from the group consisting of:

hydroxy, $C_{1-8}$ alkyloxy, and aryl $C_{0-6}$ alkyloxy.

7. A compound of claim 1 selected from the group consisting of:

N-{[6-(Piperazin-1-yl)-2,3-dihydro-1(1H)-isoindolone-2-yl]acetyl}-3(R)-methyl-b-alanine n-butyl ester; and N-{[6-(Piperazin-1-yl)-2,3-dihydro-1(1H)-isoindolone-2-yl]acetyl}-3(R)-methyl-b-alanine.

8. A composition for inhibiting the binding of fibrinogen to blood platelets in a mammal, comprising a compound of claim 1 and a pharmaceutically acceptable carrier.

9. A method for inhibiting the binding of fibrinogen to blood platelets in a mammal, comprising administering to the mammal a composition of claim 8.

10. A composition for inhibiting the aggregation of blood platelets in a mammal, comprising a compound of claim 1 in combination with two or more agents selected from a thrombolytic agent, an anticoagulant agent, and an antiplatelet agent and a pharmaceutically acceptable carrier.

11. A method for inhibiting the aggregation of blood platelets in a mammal, comprising administering to mammal the composition of claim 10.

12. A composition for inhibiting the binding of fibrinogen to blood platelets, in a mammal, comprising a compound of claim 2 and a pharmaceutically acceptable carrier.

13. A method for inhibiting the binding of fibrinogen to blood platelets in a mammal, comprising administering to the mammal a composition of claim 12.

14. A composition for inhibiting the binding of fibrinogen to blood platelets in a mammal, comprising a compound of claim 13 and a pharmaceutically acceptable carrier.

15. A method for inhibiting the binding of fibrinogen to blood platelets in a mammal, comprising administering to the mammal a composition of claim 14.

16. A composition for inhibiting the binding of fibrinogen to blood platelets in a mammal, comprising a compound of claim 4 and a pharmaceutically acceptable carrier.

17. A method for inhibiting the binding of fibrinogen to blood platelets in a mammal, comprising administering to the mammal a composition of claim 16.

18. A composition for inhibiting the binding of fibrinogen to blood platelets in a mammal, comprising a compound of claim 5 and a pharmaceutically acceptable carrier.

19. A method for inhibiting the binding of fibrinogen to blood platelets in a mammal, comprising administering to the mammal a composition of claim 18.

20. A composition for inhibiting the binding of fibrinogen to blood platelets in a mammal, comprising a compound of claim 6 and a pharmaceutically acceptable carrier.

21. A method for inhibiting the binding of fibrinogen to blood platelets in a mammal, comprising administering to the mammal a composition of claim 20.

* * * * *